(12) United States Patent
Yu et al.

(10) Patent No.: US 8,343,742 B2
(45) Date of Patent: Jan. 1, 2013

(54) ENCAPSULATION OF CELLS IN BIOLOGIC COMPATIBLE SCAFFOLDS BY COACERVATION OF CHARGED POLYMERS

(75) Inventors: Hanry Yu, Singapore (SG); Yi Chin Toh, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 183 days.

(21) Appl. No.: 12/693,300

(22) Filed: Jan. 25, 2010

(65) Prior Publication Data

US 2010/0136649 A1 Jun. 3, 2010

Related U.S. Application Data

(62) Division of application No. 10/899,899, filed on Jul. 26, 2004, now Pat. No. 7,704,714.

(51) Int. Cl.
*C12N 11/02* (2006.01)
*C12N 5/02* (2006.01)

(52) U.S. Cl. ........................... 435/182; 435/402
(58) Field of Classification Search .................. None
See application file for complete search history.

(56) References Cited

U.S. PATENT DOCUMENTS

| 6,231,879 B1 | 5/2001 | Li et al. ................... 424/422 |
| 6,916,640 B2 | 7/2005 | Yu et al. ................... 435/182 |
| 2002/0094569 A1* | 7/2002 | Yu et al. ................... 435/325 |

FOREIGN PATENT DOCUMENTS

WO WO 99/47186 A1 9/1999

OTHER PUBLICATIONS

Chia et al., (Tissue Engineering. 2000; 6(5):481-495).*
Supplemental European Search Report dated Jun. 18, 2010, in related European Application No. 05763212.7.
International Search Report for International Application No. PCT/SG2005/000249 which was mailed on Sep. 16, 2005 (3 pages).
Uludag et al., "Technology of mammalian cell encapsulation", Advanced Drug Delivery Reviews, 2000, 42: 29-64.
Renken et al., "Microencapsulation: a review of polymers and technologies with a focus on bioartificial organs", Polimery, 1998, 43: 530-539.
Sittinger et al., "Encapsulation of artificial tissues in polyelectrolyte complexes: preliminary studies", Biomaterials, 1996, 17: 1049-1051.
Toh et al., "Application of a polyelectrolyte complex coacervation method to improve seeding efficiency of bone marrow stromal cells in a 3D culture system", Biomaterials, 2005, 26: 4149-4160.
Toh et al., "A configurable three-dimensional microenvironment in a microfluidic channel for primary hepatocyte culture", ASSAY and Drug Development Technologies, 2005, 3(2): 169-176.

(Continued)

*Primary Examiner* — Cherie M Stanfield
(74) *Attorney, Agent, or Firm* — Stout, Uxa, Buyan & Mullins; Carlos A. Fisher

(57) ABSTRACT

This invention relates to a method for the encapsulation of cells in biologic compatible three dimensional scaffolds and the use of such cells encapsulated in a scaffold. The cells are embedded in a charged polymer that is complex coacervating with an oppositely charged polymer within biologic compatible scaffolds. The polymer complex embedding the cells is forming an ultra thin membrane on the surface of the three dimensional scaffold.

17 Claims, 11 Drawing Sheets

OTHER PUBLICATIONS

Botchwey et al., "Tissue engineered bone: measurement of nutrient transport in three-dimensional matrices", J. Biomed. Mat. Res. 2003 vol. 67A(1), 357-67.

Li et al., "Effects of filtration seeding on cell density, spatial distribution, and proliferation in nonwoven fibrous matrices", Biotechnol. Prog. 2001, 17, 935-44.

Kim et al., "Optimizing seeding and culture methods to engineer smooth muscle tissue on biodegradable polymer matrices", Biotechnology and Bioengineering, 1998, vol. 57(1), 46-54.

Wendt et al., "Oscillating perfusion of cell suspensions through three-dimensional scaffolds enhances cell seeding efficiency and uniformity", Biotechnology and Bioengineering, 2003, vol. 84, 205-14.

Yang et al., "Novel cell immobilization method utilizing centrifugal force to achieve high-density hepatocyte culture in porous scaffold", J. Biomed. Mater. Res. 2001, vol. 55, 379-86.

Sittinger et al., "Artificial tissues in perfusion culture", Int. J. Artif. Organs, 1997, vol. 20, 57-62 (Abstract).

Schantz et al., "Repair of calvarial defects with customized tissue-engineered bone grafts I. Evaluation of osteogenesis in a three-dimensional culture system", Tissue Engineering, vol. 9, Supp 1, 2003, 113-26.

Ushida et al., "Three dimensional seeding of chondrocytes encapsulated in collagen gel into PLLA scaffolds", Cell Transplant., 2002, vol. 11(5), 489-94.

Roberts et al., "Dopamine secretion by PC12 cells microencapsulated in a hydroxethyl methacrylate-methylmethacrylate copolymer", Biomaterials, 1996, vol. 17, 267-75.

Wen et al., "Microcapsules through polymer complexation I. Complex coacervation of polymers containing a high charge density", Biomaterials, 1991, vol. 12, 374-84.

Wen et al., "Microcapsules through polymer complexation Part 3: encapsulation and culture of human Burkitt lymphoma cells in vitro", Biomaterials, 1995, vol. 16, 325-35.

Chia et al., "Hepatocyte encapsulation for enhanced cellular functions", Tissue Engineering, 2000, vol. 6(5), 481-95.

Wallace et al., "Collagen gel systems for sustained delivery and tissue engineering", Advanced Drug Delivery Reviews, 2003, vol. 55, 1631-49.

Endres et al., "Osteogenic induction of human bone marrow-derived mesenchymal progenitor cells in novel synthetic polymer-hydrogel matrices", Tissue Engineering, 2003, vol. 9(4) 689-702.

Moran et al., "Characterization of polylactic acid-polyglycolic acid composites for cartilage tissue engineering", Tissue Engineering, 2003, vol. 9(1), 63-70.

Ringe et al., "Stem cells for regenerative medicine: advances in the engineering of tissues and organs", Naturwissenschafen, 2002, vol. 89(8), 338-51.

Bartkowiak et al., "Alginate-oligochitosan microcapsules: a mechanistic study relating membrane and capsule properties to reaction conditions", Chem. Mater., 1999, vol. 11, 2486-92.

Steadman's Medical Dictionary, 27th Ed., Lippincott Williams, 2000, "Capsule".

\* cited by examiner

Method 1

Method 2

|—————|
60 μm

|—————|
50 μm

6A

|—————|
200 μm

6B

|—————|
200 μm

6C

|—————|
200 μm

6D

|—————|
200 μm

8A

⊢―――⊣
200 μm

8B

⊢―――⊣
200 μm

8C

⊢―――⊣
200 μm

8D

⊢―――⊣
200 μm

200 μm

200 μm

ENCAPSULATION OF CELLS IN BIOLOGIC COMPATIBLE SCAFFOLDS BY COACERVATION OF CHARGED POLYMERS

This is a divisional of U.S. patent application Ser. No. 10/899,899, filed Jul. 26, 2004 (now U.S. Pat. No. 7,704,714, issued Apr. 27, 2010), the disclosure of which is hereby incorporated by reference herein in its entirety.

This invention relates to a method for the encapsulation of cells in biologic compatible scaffolds. The invention also relates to cell species encapsulated in such a scaffold, and uses of the cells encapsulated in such a scaffold.

BACKGROUND OF THE INVENTION

Scaffolds have been used extensively in the area of tissue engineering either to construct a neo-tissue that can be implanted to repair a defect site in the body or as a cell container in bioartificial devices. Scaffolds form a three dimensional matrix that serves as a template for cell proliferation and ultimately tissue formation.

Culturing cells in a scaffold typically involves seeding cells throughout the scaffold and allowing the cells to proliferate in the scaffold for a pre-determined amount of time. A lot of research efforts have been directed at the design, fabrication and choice of materials in developing a scaffold for tissue engineering applications. However, the eventual success of a scaffold will be determined by whether the scaffold is able to support cell viability and by its ability to integrate with the host tissues for implantable scaffolds. Hence, the optimization of cell seeding and culture technologies are equally important determinants in the success of a scaffold system.

A first important aspect with regard to cell seeding methods include the efficiency of the seeding method as to maximize the utilization of donor cells. Autologous cell sources are usually limited in number due to donor site morbidity hence, the ideal seeding method need to enable seeding of scaffolds with relatively low cell number at high seeding efficiency. A second important aspect is the uniform distribution of cells in the scaffold. A spatially uniform cell distribution has implications on the formation of a homogeneous tissue. Both factors influence the mass transfer within scaffolds that has been cited as one of the major limitations of culturing cells in a scaffold (Botchwey, E. A., et al., J. Biomed. Mat. Res., 2003, Vol. 67A(1), P. 357-367).

For seeding cells in scaffolds various methods have been described. So far, static seeding is the most prevalent method of seeding cells into scaffolds. For static seeding a cell suspension is seeded on a scaffold and afterwards incubated for a certain time in the absence of agitation before being exposed to dynamic culture conditions, for example into a spinner flask that is slowly agitated. However, conventional static seeding is not very efficient in delivery cells into scaffolds and often results in a very low initial cell number with low uniformity within the scaffold (Li et al., Biotechnol. Prog., 2001, Vol. 17, P. 935-944). Dynamic seeding has been investigated as a more effective alternative to static seeding. For dynamic seeding the scaffold and the cell suspension are placed together in, e.g., a tube and the tube is then incubated with gentle agitation for a certain time allowing the cells to attach to the surface of the scaffold. However, the seeding efficiency for dynamic seeding was low (from 4%-56%) and variable depending on the agitation method (Byung-Soo Kim et al., Biotechnology and Bioengineering, 1998, Vol. 57 (1), P. 46-54). Various other seeding configurations which all use some kind of active force to seed the cells into a scaffold have been developed to circumvent the limitations of static and dynamic seeding. These include filtration seeding (Li et al., 2001, supra), oscillating perfusion seeding (Wendt et al., Biotechnology and Bioengineering, 2003, Vol. 84, P. 205-214), centrifuge seeding (Yang, T. H. et al., J. Biomed. Mater. Res., 2001, Vol. 55, P. 379-386) and perfusion cartridge seeding (Sittinger et al., Int. J. Artif. Organs, 1997, Vol. 20, P. 57). However, the application of these methods are limited to scaffolds of a specific range of dimensions and pore sizes since most of the studies were performed on a single type of scaffold.

Despite the shortcomings of static seeding, this method can be employed with virtually all cell types due to its relative simplicity. Therefore, considerable efforts have been made to improve the efficiency of static seeding by using biological hydrogels such as fibrin glue (Schantz et al., Tissue Eng., 2003, Vol. 9, Suppl.1, P. 113-126) and collagen (Ushida et al., Cell Transplant., 2002, Vol. 11(5), P. 489-494). However, the extent of gelation (complexation) of such hydrogels cannot be controlled very well owing to the inherent variability in biological materials and there is no precise control over the physiochemical parameters that triggers the gelation of these biological hydrogels. This may have implications on the diffusion limits of nutrients inside the scaffolds. Sufficient gelation can effectively trap the cells inside the scaffolds but often limit the diffusion. On the other hand, insufficient gelation will be good for mass transfer but not improving the cell seeding efficiency.

Thus, there remains a need for an effective seeding of cells in scaffolds.

SUMMARY OF THE INVENTION

In one aspect, the present invention provides a method for encapsulating at least one cell species in a biologic compatible scaffold. A method for encapsulating at least one cell species in a biologic compatible scaffold comprising:

(a) providing a first substrate coated with a first charged polymer;

(b) placing a scaffold comprising at least one cell species embedded in a second charged polymer having an electrical charge opposite to that onto the first charged polymer on the first substrate;

(c) placing a second substrate coated with a third charged polymer to form a sandwich structure with the first substrate and the scaffold arranged there in between, wherein the first polymer and the third polymer are of the same electrical charge.

Using this method different attachment-dependent or attachment-independent cells can be encapsulated on the surface of a three dimensional scaffold to achieve a more effective seeding even with low initial cell numbers and a homogenous distribution of the cells within the scaffold. The cells are embedded in an ultra thin membrane formed by coacervation of the oppositely charged polymers to form a polymer complex. This polymer complex creates polymer fibers that form the basic structure of a polymer matrix in which the cells are embedded. Due to the ultra thin membrane cells are entrapped within the scaffold and cannot be washed out of the scaffolds so easily. As the cells are not attached directly to the surface of the scaffold but embedded in an ultra thin membrane that is attached to the scaffold, the method of the present invention is independent of the material and size of the scaffold used.

Other aspects and advantages of the invention will become apparent from the following detailed description, taken in conjunction with the accompanying drawings and examples, which illustrate by way of example, the principles of the invention.

BRIEF DESCRIPTION OF THE DRAWINGS

In FIG. 1 a cell containing scaffold (3) that is embedded in a second charged polymer is sandwiched between a first substrate (4) and a second substrate (1). The first substrate (4) is coated with a first charged polymer (5) and the second substrate (1) is coated with a third charged polymer (2).

FIGS. 6A and 6B show the front and backside sections of the Cytomatrix™ scaffold that was encapsulated by complex coacervation. FIGS. 6C and 6D shows the front and backside sections of the control scaffold.

FIG. 8D shows a control scaffold that was seeded by conventional static seeding (method) (for more details see Example 3).

FIGS. 16D and E show different sides of a control scaffold seeded by conventional seeding (methods) (for more details see Example 5).

FIGS. 17A and B show the front and back side of a scaffold in which cells are encapsulated according to the method of the present invention, respectively. FIGS. 17C and D show the front and back side of a control scaffold in which cells are encapsulated using standard static seeding (methods), respectively.

DETAILED DESCRIPTION OF THE INVENTION

Figure 1:
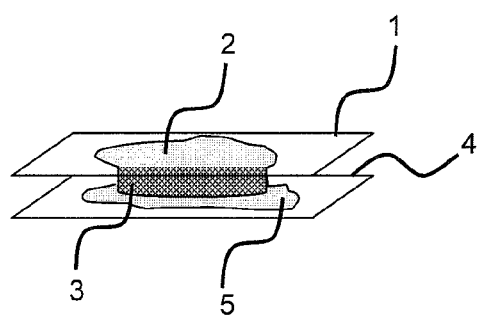
FIG. 1 shows a schematic picture of the claimed method of encapsulating cells within the confines of a scaffold.

In the method of the present invention at least one cell species is encapsulated in a biologic compatible scaffold. This method that is depicted in FIG. 1 comprises:
(a) providing a first substrate (4) coated with a first charged polymer (5);

(b) placing a scaffold comprising at least one cell species embedded in a second charged polymer (3) having a charge opposite to that onto the first charged polymer (5) on the first substrate (4);

(c) placing a second substrate (1) coated with a third charged polymer (2) to form a sandwich structure with the first substrate (4) and the scaffold (3) arranged there in between, wherein the first polymer (5) and the third polymer (2) are of the same electrical charge.

The polymer complex forms a permeable, biologic compatible ultra thin membrane that allows living cells embedded therein to remain viable, yet protects the cells against, e.g., immunological rejection by the host since the membrane is impermeable to bacteria, lymphocytes, large proteins and other entities of the type responsible for immunological reactions. This ultra thin membrane is formed by complex coacervation of the second charged polymer with the first and third charged polymer. Being soluble in water, charged polymers offer the feasibility of developing an aqueous encapsulation system that is compatible with the cellular milieu. Besides eucaryotic cells such as mammalian cells, insect cells, amphibian cells, plant cells, and yeast cells the method of the present invention can also be used to cultivate prokaryotic cells. The prokaryotic cells may be selected from, but not limited to, the genus *Escherichia, Bacillus* or *Lactococcus*. Some examples of prokaryotic cell species from these genera are *Escherichia coli, Bacillus subtilis* or *Lactococcus lactis*.

As used in the present invention the term "encapsulation" means to entrap cells within the boundaries (confines) of a scaffold, wherein the surface of the scaffold is covered by a ultra-thin polymer layer in which the cells are embedded. The "surface" of the scaffold is formed by the polymer fibers building up the system of continuous interconnected pores of the scaffold. For example, the surface of the Cytomatrix™ scaffold used in an example of the present invention is made out of niobium-coated carbon. Accordingly, the method of the present invention is a combination of methods typically known as microencapsulation and macroencapsulation (see for example, Uludag et al., Advanced Drug Delivery Reviews, 2000, Vol. 42, P. 29-64). In microencapsulation (methods) a smaller cell mass is individually entrapped in its own spherical polymer capsule (with a diameter Ø=of about 0.3 to about 1.5 mm, for example) or layer. In macrocapsulation (methods) cells are enclosed between two or more selectively permeable flat sheet membranes or within the lumen of a semipermeable hollow fiber. In the present invention cells are microencapsulated in a polymer complex that is macroencapsulated in a scaffold to achieve a high seeding efficiency.

Using the method of the present invention allows to overcome the disadvantages of conventional static scaffold seeding methods described above. The seeding efficiency using the method of the present invention was found to be 94.1%±2.7% (see Example 1) and thus much higher than the seeding efficiency of static seeding methods described in the state of the art. For example the seeding efficiency described by Li et al. (Biotechnol. Prog., 2001, Vol. 17, P. 935-944) was reported to be <40%.

Furthermore, comparative encapsulation experiments using other methods shows that the polymer complex formed according to the method of the present invention is distributed more homogenously within the whole scaffold (FIG. 5), which is imperative for the formation of a homogenous cell culture or homogenous tissue within the scaffold. Example 6 shows that the distribution of cells within the scaffold seeded according to the method of the present invention is more uniform than conventional seeding (methods).

Figure 2:
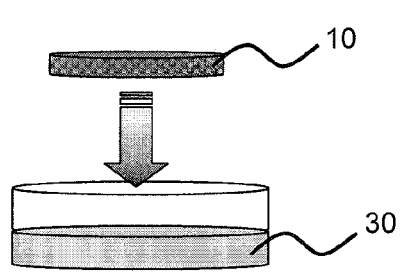
FIG. 2 shows two different methods for encapsulating cells in scaffolds as described in Example 2. In Method 1, a scaffold containing the first charged polymer (10) is dipped into a reservoir containing the first charged polymer (30) to complex coacervate. In Method 2, a second charged polymer (40) is delivered into the middle of the scaffold (20) via a needle of a syringe (50) until the first charged polymer (30) is displaced from the scaffold.
Figure 2:
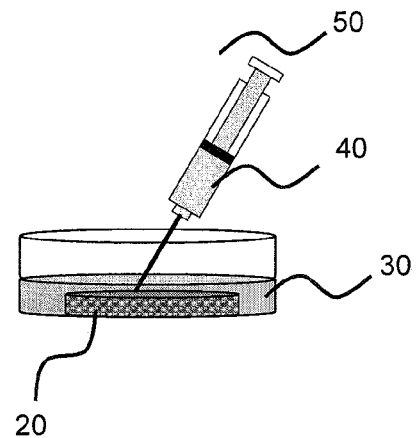
Figure 3:
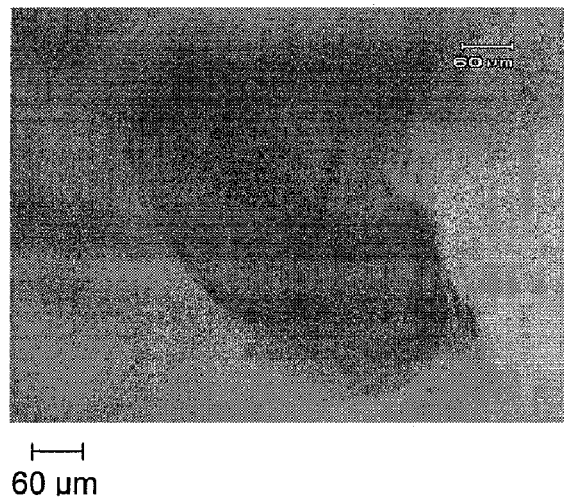
FIG. 3 shows a phase contrast image of a collagen-terpolymer complex (stained with trypan blue) that was formed outside the scaffold in a terpolymer solution which terpolymer-collagen solution was used to encapsulate the Cytomatrix™ scaffold using method 1 as depicted in FIG. 2 and described in more detail in Example 2.
Figure 4:
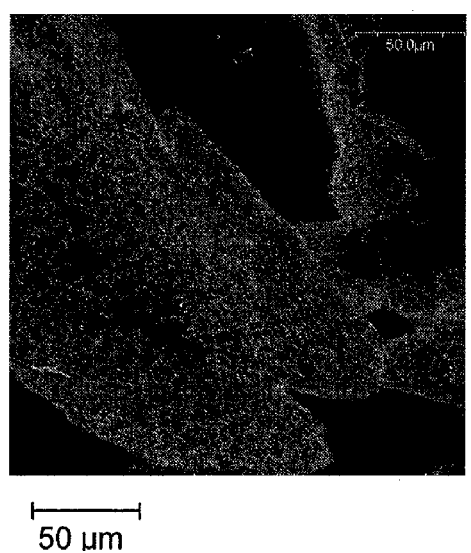
FIG. 4 shows a back-scattering confocal image (60× magnification) of collagen-terpolymer complexes formed inside the Cytomatrix™ scaffolds using method 2 as depicted in FIG. 2 and described in more detail in Example 2.

The comparative experiments include two further methods. In method 1 depicted in FIG. 2 a second charged polymer is aliquoted into a scaffold. The scaffold containing the second charged polymer (10) was then gently dipped into a reservoir containing the first charged polymer (30) for complex coacervation. Using this method it was observed that the majority of the second charged polymer has been displaced out of the scaffold and complex coacervated with the first charged polymer (30) (FIG. 3) outside the scaffold. In method 2 (FIG. 2) the scaffold was first placed into a reservoir containing the first charged polymer (30). The second charged polymer (40) was then delivered into the middle of the scaffold (20) over a needle of a syringe (50) until the first charged polymer (30) was displaced out of the scaffold. The polymer complex was formed within the scaffold. However, the distribution of the complex within the scaffold using method 2 was not uniform as can be seen in FIG. 4.

The polymer complexes formed in the present invention are permeable to substances necessary to sustain the normal metabolic functions of the at least one cell species and to products released by the at least one cell species. The polymer complex is formed upon the reaction of the second charged polymer containing the at least one cell species with the first (5) and third (2) charged polymer in the scaffold, wherein the first (5) and third (2) charged polymer have a sufficient charge density to coacervate with an oppositely-charged second polymer to form an ultra thin membrane at physiologic pH. This membrane may have a thickness of 2-10 µm or 2-3 µm, for example, but is not limited thereto and can accordingly be thinner or thicker.

Both, naturally occurring and modified polymers are suitable for use as charged polymers in the practice of the present invention. In this connection it is noted that the term "electrical charge" means that the polymers carry a net charge, i.e. are either positively or negatively charged, when present in a solution. Accordingly, the term that "two polymers are of the same electrical charge" means that they both carry an either positive or negative net charge the exact value of which (expressed for example in Coulomb) can be different. Thus, the term "of the same electrical charge" has to be understood qualitatively and not quantitatively.

The polymers used in the present invention are typically water-soluble and in addition usually have a molecular weight of at least 3000 Da. Another advantage of using the complex coacervation according to the present invention is that the polymer complex encapsulating the cells is formed without the use of organic solvents that are often harmful to the encapsulated cells (Roberts T. et al.; Biomaterials; 1996; Vol. 17, P. 267-275). It is possible that the first and third polymer as used herein are negatively charged. In such a case, the second polymer is of course positively charged. Alternatively, the first and third polymer are positively charged and the second polymer carries a negative net charge.

The first and third charged polymer can be of different chemical composition or nature. In one embodiment of the present invention, the third charged polymer and the first charged polymer are identical.

Polymers that are suitable for the use in the present invention include chitosan, polyanionic alginate, positively charged (e.g. methylated collagen) collagen, negatively charged collagen, polyanionic alginate, $Ca^{2+}$, or synthetic polymers such as polycationic poly(L-lysine) and co-polymers or terpolymers that include poly(acrylic acid), poly (methacrylic acid), poly(methacrylate) or poly(methyl acrylate) to name only a few. A useful terpolymer may consists of two polymer blocks containing at least one of acrylic acid and methacrylic acid and at least one of hydroxyethyl methacrylate and hydroxylpropyl methacrylate. Such terpolymers can consist of about 10%-50% hydroxyethyl methacrylate, about 10%-50% methacrylic acid and about 50% methyl methacrylate (HEMA-MAA-MMA). An example for such a terpolymer consists of 25% hydroxyethyl methacrylate, about 25% methacrylic acid and about 50% methyl methacrylate (HEMA-MAA-MMA) (Chia et al., Tissue Engineering 2000, Vol. 6(5), P. 481-495). In another example the terpolymer consists of 25% hydroxyethyl methacrylate, about 50% methacrylic acid and about 25% methyl methacrylate (HEMA-MAA-MMA). Other terpolymers that can be used in the method of the present invention are described by Shao Wen et al. who used terpolymers of different compositions for embedding living cells (Shao Wen, Yin Xiaonan and W. T. K. Stevenson, Biomaterials, 1991, Vol. 12 May, P. 374-384; Shao Wen, H. Alexander et al., Biomaterials, 1995, Vol. 16, P. 325-335). These terpolymers consist of HEMA-MMA-MAA or HEMA-MMA-DMAEMA (cationic 2-(dimethylamino) ethyl methacrylate) whereas the latter terpolymer is positively charged.

Combinations of polymers from this group can be used to form a polymer complex for embedding living cells by coacervation. In one embodiment of the present invention the third charged polymer and the first charged polymer which form the polymer complex by reacting with the second charged polymer are identical. Exemplary combinations of polymers in which the first and third charged polymer are reacted with the second charged polymer include the following (wherein the second charged polymer is mentioned first, followed by the first/third charged polymer: chitosan-terpolymer (Example 5), polyanionic alginate-$Ca^{2+}$, positively charged collagen-terpolymer (Example 1 to 4), negatively charged collagen-positively charged terpolymer (Shao Wen, Yin Xiaonan and W. T. K. Stevenson, Biomaterials, 1991, Vol. 12 May, P. 374-384), polyanionic alginate-polycationic poly(L-lysine).

Since polymers such as collagen are in their natural form neither positively nor negatively charged they need to be modified for use in the present invention. Techniques to modify such polymers are known in the state of the art. In Chia et al. for example (Tissue Engineering, 2000, Vol. 6 (5), P. 481-495) cationic collagen was obtained by esterification of the carboxyl groups with low-molecular-weight alcohol. Negatively charged collagen can, for example, be obtained by the method described by Donald G. Wallace and Joel Rosenblatt (Advanced Drug Delivery Reviews 2003, Vol. 55, P. 1631-1649). Other examples of an uncharged polymer that can be modified to carry an electrical net charge include, but are not limited to poly (vinyl alcohol) and further polysaccharides such as dextrans and polysaccharides of the carrageenan family (obtained from the red seaweeds).

Optionally, polymers that are naturally charged can be modified to (better) match the electrical charge of the oppositely charged polymer that is used as reaction partner. The different electrical charge can also be used to influence the permeability of the ultra thin membrane. Large differences in charge densities between the oppositely charged polymers tend to make the membrane more permeable.

As the encapsulation isolates the cells physically from the culture media that flows through the scaffold, it is necessary for the cells that the membrane formed by the polymer complex is permeable to nutrients that are imperative for the survival of the embedded cells. By varying the molecular weight, the charge density and the concentration of the charged polymers as well as the reaction time (contact time) between the oppositely charged polymers, the permeability and transport properties of the membrane can be modulated.

The influence of different charge densities on the formation of the polymer matrix and their respective effect on the functionality of the embedded cells is demonstrated by modulating the charge density of collagen that is used as second charged polymer. Using the method described by Chia et al. (Tissue Engineering 2000, Vol. 6, P. 481-495) type I bovine dermal collagen (Vitrogen, Cohesion Technologies Inc., Palo Alto, Calif.) methylation renders collagen cationic.

The degree of methylation is controlled by adjusting the reaction time and temperature of a polymer as described in Example 4. The methylation degree is determined using a capillary zone electrophoresis method that was developed by the inventors and is described in Example 4. Using this new method a CE index is proposed by the inventors to monitor the degree of methylation of a polymer used in the method of the present invention. An increase in polymer methylation is correlated with an increase in this CE index. For example, a slightly methylated polymer has a CE index of about between 0.9 and about 1.7 whereas a highly methylated polymer has a CE index of about between 1.7 and about 2.5.

Figure 10:
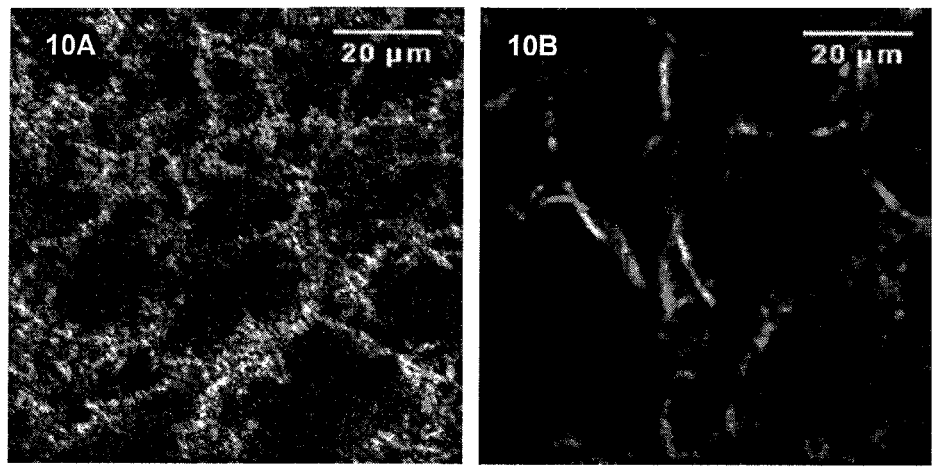
FIG. 10 illustrates the effect of different kinds of collagen methylation on collagen matrix formation (Example 4). Representative images of collagen matrices formed with 3 wt % terpolymer: (A) Slightly methylated collagen (CE index 1.4); (B) Highly methylated collagen (CE index between 1.9).

When a slightly methylated collagen (CE index 1.4) is used to react with a first charged polymer, e.g. HEMA-MMA-MAA, the matrix formed upon reaction of the polymers consists of more cross linked and thicker fibers as can be seen from FIG. 10A. On the other hand using highly methylated collagen (CE index 1.9) leads to lesser cross linked and thinner fibers as can be seen from FIG. 10B. Therefore, an increase in collagen methylation can be correlated with more fragmented matrix morphology as can also be seen from FIGS. 11A and 11B which compare the mean dendritic length and dendrite number formed by slightly and highly methylated collagen (11A Mean dendritic length per node; 11B Mean dendrite number per node [(□) slightly methylated collagen; (Δ) highly methylated collagen]).

Figure 13:
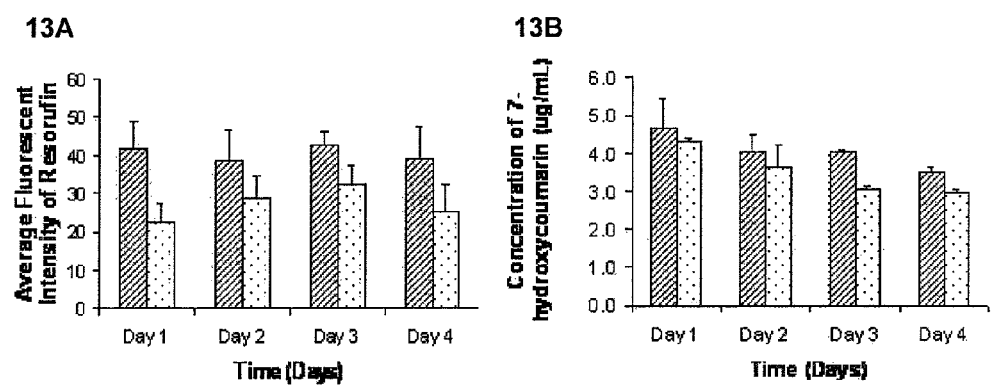
FIG. 13 illustrates the effect of collagen methylation on hepatocyte detoxification cytochrome P450-dependent monooxygenase activities (Example 4). (A) 7-ethoxyresorufin-O-dealkylation (EROD) activity, as quantified by the average fluorescent intensity of resorufin; (B) 7-ethyoxycoumarin-O-deethylase (ECOD) activity, as quantified by the concentration of 7-hydroxycoumarin. [(▒) Slightly methylated collagen; (■) Highly methylated collagen].

The polymer matrix formed by different methylated collagen influences the functionality of the cells embedded therein. As described in Example 4, detoxification functions of primary hepatocytes are influenced depending on whether they are embedded in slightly (CE index 1.4) or highly (CE index 1.9) methylated collagen. The detoxification activity of primary hepatocytes was higher when slightly methylated collagen is used to form the polymer matrix (FIGS. 13A and 13B). In contrast, amplification of HepG2 cells was greater in highly methylated collagen than in slightly methylated collagen.

Therefore, the proposed method of controlling the formation of the polymer complex by influencing the charge density on a polymer was demonstrated to be capable of modulating the matrix morphology to provide differential levels of cellular support. In particular, the precise control of the polymer matrix supporting live cells is important in cellular support and functions because the cell functions were selectively augmented in matrices with different fiber cross linking.

Figure 7:
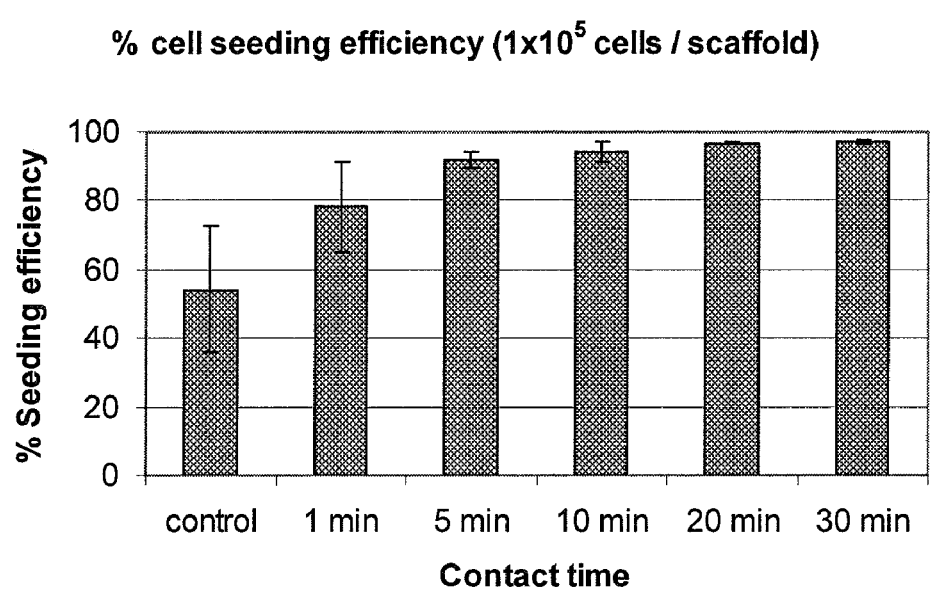
FIG. 7 shows the percentage seeding efficiency of pig bone marrow stroma cells in Cytomatrix™ scaffolds by encapsulation of positively charged collagen and terpolymer at different polymer contact times (for more details see Example 3).

Altering the contact time between the reacting oppositely charged polymers provides another option to influence the characteristics of the polymer matrix formed. By varying the contact time, the density of the modified polymer complex can be altered, as described in Example 3. The experiments show that the seeding efficiency is increased up to 43% compared to the seeding efficiency with conventional static seeding (methods) when longer contact times for the polymers are applied (FIG. 7). Compared to dynamic seeding (methods) it was demonstrated that a longer contact time has no negative influence on cell viability as can be seen from FIG. 9. Typical contact times used in the method of the present invention (after forming the sandwich structure as described above) range between from about several seconds, for example about 10 or about 30 second to about 1 hour or even longer. In some embodiments, the contact time between the two substrates supporting the charged polymers and the scaffold varies between about 30 seconds to about 30 minutes or about 45 minutes. By diluting the charged polymers which have not reacted to form a polymer complex with a suitable liquid media, the reaction is stopped using phosphate buffered saline (PBS, pH 7.0) or a cell culture media like Dulbecco's Modified Eagle Medium (DMEM) or modified Chee's medium (HeptaoZYM-Serum Free Media from Gibco BRL). It is within the discretion of the skilled artisan to determine how the composition of the polymer matrix forming the ultra thin membrane needs to be modified to meet the requirements of different cell species. Compared to other methods known in the state of the art as described above for seeding cells into scaffolds, polymer complex coacervation as described here allows a better control of the composition of the coacervated membrane in which the cells are embedded. A higher density of the polymer complex, for example, yields a higher resistivity of the membrane against shear forces that arise due to fluid movement in dynamic culture methods. Therefore, the encapsulation method of the present invention allows to seed cells into scaffolds that can be used under static culture as well as under dynamic culture conditions.

The substrates used that are coated with the electrically charged polymers and/or support the employed scaffold can be made of any material that provide sufficient mechanical support for the scaffold and are inert towards the materials. Suitable substrates may comprise or consist of glass, plastic, silicon, a metal or metal oxides, to name only a few. Plastic substrate may be made from polycarbonate, polystryrene, polypropylene or other materials which are typically used for manufacture of ELISA plates or Petri dishes and other equipment used in cell culture research. The substrate can also be a glass cover slip or a sheet of paper. Typically, the substrates are planar.

In principle, any cell species that can be cultivated in vitro, can be encapsulated in a scaffold using the method of the invention. Typically, cell species used can be subdivided in attachment-dependent and attachment-independent cells. The method of the present invention is very suitable for the expansion of both types of such cells in three dimensional cell culture systems. Examples of attachment-dependent cell species that can be encapsulated in a scaffold according to the method of the present invention include, but are not limited to bone marrow stroma cells, calvarial osteoblasts, Langerhans cells, hepatocytes, chondrocytes, cardiac myocytes, sinusoidal endothelial cells, dermal fibroblasts, keratinocytes and oligodendrocytes. Attachment-independent cells can be encapsulated together or without attachment-dependent cells. Examples for attachment-independent cell species that can be encapsulated in a scaffold according to the method of the present invention include, but are not limited to hematopoetic stem cells, T-lymphocytes, macrophages and neutrophils.

The scaffolds used in the present invention comprise a reticulated structure of interconnected pores. The pores being of size that permits the cells embedded in the second charged polymer to be attached to the cell pores and fixed there by forming a polymer complex due to a complex coacervation reaction. One useful aspect of the scaffolds used in the present invention is their penetrability for the cell medium that is necessary to transport nutrients and metabolites to and from the cells encapsulated within the scaffold. Internal fluid perfusion within the scaffold is increasing rapidly with increased pore volume an pore diameter. Therefore, the pore density of the scaffolds used in the present invention is varying between 20 and 95% to adjust the medium flow within the scaffold according to the requirements of the cell specie(s) used.

Depending on the use of the claimed method, scaffold material and polymers used for complex coacervation can be biodegradable. To use biodegradable material is especially advantageous, e.g., for tissue engineering wherein the scaffolds containing the cells are used to repair defect sites in living tissue, e.g. bone. Due to the fact that the formation of the ultra thin membrane is independent of the material of the three-dimensional scaffold, a high variety of scaffolds can be used dependent on the application. Scaffolds comprise or are made from agarose, polycaprolactone (Endres, M. et al., Tissue Engineering, 2003, Vol. 9, No. 4, P. 689-702), niobium coated carbon, chitosan, hydroxyapatite-tricalcium phosphate (Harris, C. T. and Cooper, L. F., Comparison of matrices for hMSC delivery, 2004, P. 747-755), collagen, hyaluronic acid, calcium phosphate, starch, hydroxyapatite, fibrin, alginate, poly-glycolic acid, carbon nano fibres, polytetrafluoroethylene, polylactic acid (Moran, J. et al., Tissue Engineering, 2003, Vol. 9, No. 1, P. 63-70) and mixtures thereof, for example. Foam scaffold as those described in U.S. Pat. No. 6,231,879 which are based on thermoplastic elastomers such as polyamide, polyester, polyethylene polyvinylidene fluoride, polyethyurethane or silicone can also be used in the present invention.

The scaffold in which the cell species are encapsulated can have a regular or an irregular (outer) shape. If the scaffolds are, e.g., used in tissue engineering the shape of the scaffold will fit the shape of the defect side in which the scaffold will be implanted. A scaffold with a regular shape can be rectangular, a square, or of polyhedric or spherical shape. Scaffold of a rectangular shape usually have a length in their largest dimension of about 1 mm to about 5 cm. Spherical scaffolds typically have a diameter in the range between about 1 mm to about 5 cm.

The present invention can be used for a wide variety of applications, e.g. tissue engineering. It can be used, e.g., for the three dimensional expansion of autologous cells like bone marrow mesenchymal stem cells which are limited due to donor site morbidity. The host for such applications may be any suitable animal. In a further embodiment said host is a mammal or a human patient.

The claimed method can also be used as a three dimensional in vitro culture system for attachment-dependent cells, e.g., hepatocytes in a three dimensional microenvironment which mimics the physiological microenvironment more closely. This method is also advantageous because the ultra thin membrane formed by complex coacervation can be readily broken to allow gentle harvest of cells from the scaffold. The ultra thin membrane can be broken by solutions containing dissociation enzymes. Examples for such solutions are collagenase, trypsin that was used in Example 5 or the commercially available solution Accumax (Innovative Cell Technologies Inc. San Diego, Calif.) which is comprised of collagenase and proteases. The kind of cell dissociation solution used depends on the polymers used to encapsulate the cells in the scaffold.

Example 1

The following example describes the encapsulation of goat bone marrow stroma cells (BMSCs) into Cytomatrix™ scaffolds (Cytomatrix LLC, Woburn, Mass.) by the complex coacervation between modified collagen and terpolymer of hydroxylethyl methacrylate-methyl methacrylate-methyl acrylic acid (HEMA-MMA-MAA).

In this example, the Cytomatrix™ scaffold is used as a three dimensional cell growth scaffold to assess the feasibility of encapsulating goat BMSCs by complex coacervation. The Cytomatrix™ scaffold is composed of biocompatible niobium-coated carbon with a thickness of about 3 mm and a diameter of about 9 mm. It has a regular, dodecahedral inner structure with continuous interconnected pores with a porosity of greater than 90%. Therefore, the Cytomatrix™ scaffold provides a microenvironment mimicking that of the bone marrow. Hence, the biomimetic three-dimensional microenvironment of the Cytomatrix™ scaffold should be suitable for the proliferation of the goat BMSCs.

The charged polymers used to encapsulate the BMSCs in the three-dimensional scaffold are modified collagen (4° C., 6 days modified) and terpolymer of HEMA-MMA-MAA obtained by the method described by Ser-Mien Chia et al. 2000 (supra).

Collagen can be modified to be cationic and anionic by the removal of either the negative or the positive charge from the collagen chains. In this example the cationic collagen was obtained through the modification of the carboxyl group by esterification with low molecular weight alcohol as described as follows.

A total of 20 ml of stock solution (3 mg/ml) of collagen (Vitrogen 100, Collagen Corp., Palo Alto, Calif.) can first be precipitated with 400 ml of acetone. The precipitated collagen is dissolved in 200 ml of 0.1 M HCl containing methanol (Merck), and stirred at 4° C. for 6 days under sterile conditions. The modified collagen solution is then dialyzed against distilled water for an additional 4 days at 4° C. followed by freeze-drying. The lyophilized modified collagen can then be stored up to 6 months at −20° C. in the presence of desiccant. The modification is monitored by titration.

The concentration of modified collagen used can be 1.5 mg/ml. The terpolymers of MAA, HEMA, and MMA can be synthesized by solution polymerisation in 2-propanol using 2,2'-azobisisobutyronitrile (AIBN) as initiator. The monomers are distilled under nitrogen at reduced pressure. The polymerisation is performed with an initiator concentration of 0.1 mol % of monomers under nitrogen with a magnetic stirrer at 78° C. in an oil bath. The feed ratio of MAA, HEMA, and MMA are fixed at 25:25:50 (mol/mol) or other ratios as desired (such as 25:50:25) and the ratio of total monomer to solvent at 1:6 (wt/vol). The reaction is allowed to proceed for overnight and quenched by cooling to room temperature. The polymer is precipitated by addition to a large excess of petroleum ether. The precipitate is redissolved in a minimum volume of ethanol, and reprecipitated in distilled water. Recovered polymer is then dissolved in a 1 M sodium hydroxide solution, and further purified by repeated dialysis against distilled water with molecular-weight cut-off (MWCO) of 3,500, and lyophilised. The yield of the polymer are found to be ~63% for the terpolymer with 25% MAA:25% HEMA: 50% MMA. The polymer composition is determined by proton nuclear magnetic resonance (NMR) and the actual ratio of MAA, HEMA, and MAA is found to be 20.4:27.4:52.2 (mol/mol) for the feed ratio of 25:25:50 and 20.0:56.0:24.0 (mol/mol) for the feed ratio of 25:50:25. The molecular weights of the terpolymer after dialysis determined by gel permeation chromatography [with tetrahydrofuran (THF) as eluent] are about 113,00 and 373,00, respectively. 3% terpolymer was used to encapsulate the cells in the three-dimensional scaffolds. The HEMA-MMA-MAA polymer has been used because of its advantageous characteristics. The MAA added into the terpolymer enhances the water solubility of the polymer, allowing the entire encapsulation to be carried out in an aqueous environment. MMA is providing the mechanical strength, toughness and elasticity of the ultra thin membrane.

Goat BMSCs were used in this experiment to assess the efficacy of using complex coacervated encapsulation to seed cells into three-dimensional scaffolds. BMSCs are anchorage dependent cells that have potential clinical and research applications as they are capable of differentiating into lineages of the mesenchymal tissues, including bone, cartilage, fat and muscle (Ringe et al., Naturwissenschaften, 2002, Vol. 89 (8), P. 338-351). However, their expansion in two-dimensional cultures is limited and this problem is compounded by the fact that these cells rapidly lose their ability to proliferate and differentiate after multiple passages. Goat BMSCs (P7) were obtained from previously frozen samples and cultured using Dulbecco's modified Eagle medium (DMEM), low glucose (Gibco) supplemented with 10% fetal bovine serum (FBS). The cultures were cultured to about 80% confluence before passaging.

For the preparation of encapsulated goat BMSCs in Cytomatrix™ scaffolds $5 \times 10^5$ cells/ml of goat BMSCs were mixed with 1.5 mg/ml of modified (methylated) collagen and 100 μl of the cell-collagen mixture was seeded into each scaffold (3). Encapsulation was carried out by spreading a thin layer of 3% terpolymer solution (5) on a glass cover slip as first substrate (4) and placing the cell-collagen filled scaffold (3) onto the glass cover slip (4). A second glass cover slip which was used as second substrate (1) with a thin layer of terpolymer solution (2) was placed on top of the scaffold such that the scaffold was sandwiched between two layers of terpolymer (FIG. 1). After 10 minutes contacting time, the complex coacervation reaction was quenched with PBS solution. The scaffolds were then transferred into spinner flasks for dynamic culturing at 2 rpm for 2 weeks.

Controls were established by conventional static seeding. $5 \times 10^5$ cells/ml of cells were resuspended in medium and 100 μl of cell suspension was seeded into each scaffold. The scaffold was then incubated at 37° C. for 4 hours to allow for cell attachment before placing into spinner flasks for dynamic culturing (Method provided by Cell Sciences Pte Ltd., Singapore, www.cordlife.com).

The seeding efficiency of the present method of static seeding by encapsulation is determined by quantifying the number of cells that remained in the reaction well after quenching the complex coacervation reaction. Cell viability is assessed after 2 weeks of culture by Cell Tracker Green (CTG, Molecular Probes Inc., Oregon) and Propidium Iodide (PI, Molecular Probes Inc., Oregon) staining. Specimens are prepared by staining viable cells green with the fluorescent dye, CTG. The matrices are incubated at 37° C. with 20 μM CTG in culture medium for 30 minutes. After rinsing twice with PBS, each sample is then placed in 0.1 mg/ml Propidium Iodide solution for 2 minutes at room temperature to stain dead cells red. The matrices are then rinsed twice in PBS and 300 μm sections on both sides of the scaffold have been viewed under the confocal laser microscope (Olympus Fluoview 500) at 488 nm and 543 nm excitation.

Figure 6:
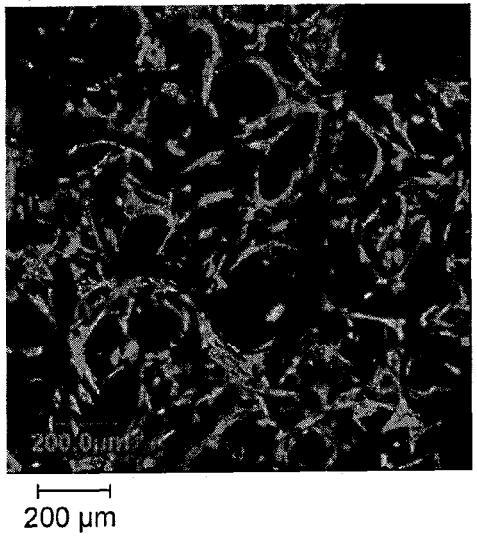
FIG. 6 shows a cell tracker green and propidium iodide (CTG/PI) staining of goat bone marrow stroma cells after two weeks of culture in a scaffold (Example 1). Images shown are projections of a 300 µm optical section (z-axis, i.e. longitudinal axis of the cylindrical scaffold) onto a single plane (10× magnification).
Figure 6:
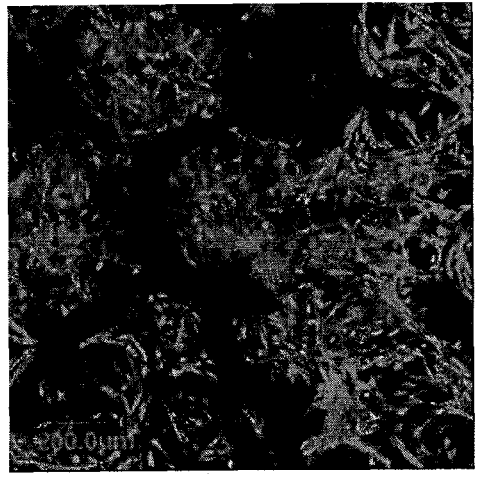
Figure 6:
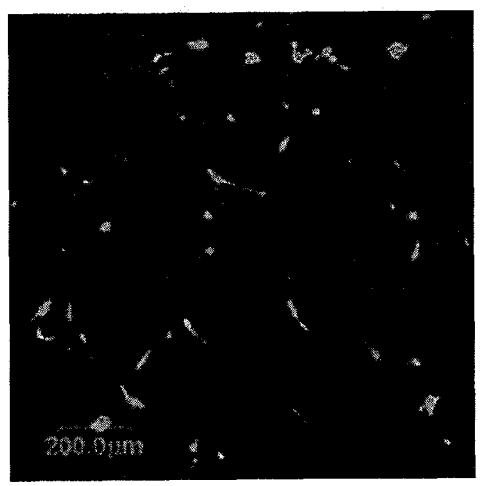
Figure 6:
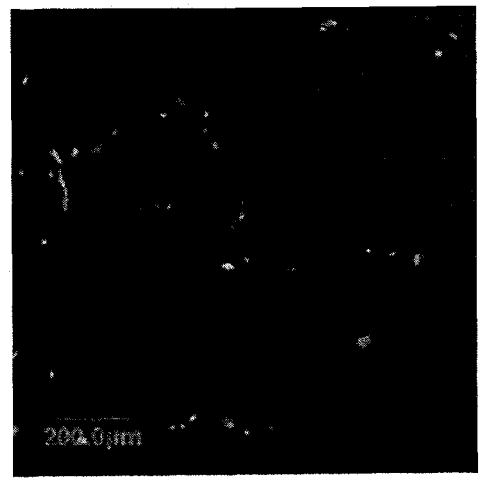

The seeding efficiency by encapsulation is found to be 94.1%±2.7%. This seeding efficiency is much higher than conventional static seeding which is reported to be <40% (Yan Li et al., Biotechnol. Prog., 2001, Vol. 17, P. 935-944). The high seeding efficiency of the proposed cell seeding method by encapsulation in turn is translated into higher cell number at the end of the culture period. The differences can be seen from the 300 μm sections of both sides of the scaffold. FIGS. 6 A and B shows the front and back side of the scaffold seeded with the method of the present invention whereas FIGS. 6C and D shows the front and backside of the control scaffold seeded with the conventional static seeding method as described above. By controlling the density of the complex coacervated matrix, enhanced cell seeding efficiency can be achieved without compromising on the cell viability. Moreover, the entrapment of goat BMSCs into three dimensional scaffolds by encapsulation also resulted in more uniform cell distribution in the circumferential plane than conventional static seeding as can be seen in FIG. 6 (supra). The disclosed method of static seeding into three dimensional scaffolds by encapsulation has been demonstrated to be effective in entrapping cells into three dimensional scaffolds while providing a suitable environment for maintaining cell viability.

Example 2

The following example describes the comparative experiments that are carried out to compare different methods of encapsulating cells in Cytomatrix™ scaffolds with charged polymers.

In this example, it is attempted to fill the three dimensional Cytomatrix scaffolds with 1.5 mg/ml of modified collagen and encapsulate the scaffold using 2.5% of terpolymer solution. Modified collagen and terpolymer solution are obtained as described in Example 1. In addition to the method of the present invention (FIG. 1), two further methods are used and described as follows (FIG. 2):

Method 1

100 µl of 1.5 mg/ml of modified collagen is aliquoted into the Cytomatrix™ scaffold (10) and the scaffold is gently dipped into a reservoir of 2.5% terpolymer solution (30).

Method 2

The Cytomatrix™ scaffold (20) is first placed into a reservoir of 2.5% terpolymer solution (30). 1.5 mg/ml of modified collagen (40) is then delivered into the middle of the scaffold using a syringe with a 25.5 G needle (50) until the terpolymer solution (30) is displaced out of the scaffold (20).

Method of the Invention

Encapsulation is carried out by spreading a thin layer of 2.5% terpolymer solution (5) on a coverslip (4) and placing the collagen filled scaffold (3) onto the coverslip (4). A second coverslip (1) with a thin layer of terpolymer solution (2) is placed on top of the scaffold (3) such that the scaffold is sandwiched between two layers of terpolymer.

For method 1, scaffolds are observed to be empty under phase contrast microscopy. To determine whether the collagen solution has been displaced out of the scaffold into the terpolymer solution, trypan blue is added to the terpolymer solution that is used to encapsulate the scaffold since trypan blue will stain collagen preferentially. It can be observed that the majority of the collagen has been displaced out the scaffold and complex coacervated with the terpolymer outside the scaffold (FIG. 3).

Figure 5:
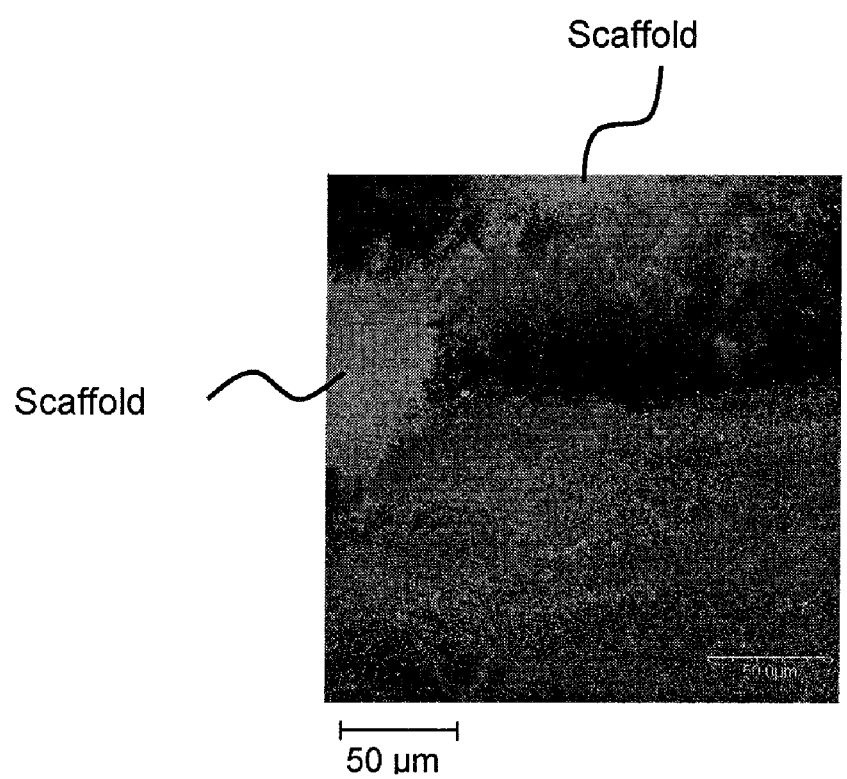
FIG. 5 shows a back-scattering confocal image (60× magnification) of collagen-terpolymer complexes formed inside the Cytomatrix™ scaffolds using the method of the present invention as depicted in FIG. 1 and described in more detail further below.

For method 2 and the method according to the present invention, collagen-terpolymer complexes are formed within the scaffold. However, the distribution of the complex within the scaffold using method 2 is not very uniform. Pockets of collagen-terpolymer complexes with distinct interface are formed inside the scaffold as terpolymer solution is displaced by collagen solution that is being injected into the scaffold. (FIG. 4). Collagen-terpolymer complex distribution with the scaffold is much more uniform in the method of the present invention since terpolymer solution only comes into contact with the modified collagen solution at the surface of the scaffold (FIG. 5). Henceforth, the method according to the present invention is used for the encapsulation of cells in the three dimensional scaffolds.

Example 3

The following experiment describes the encapsulation of pig bone marrow stroma cells (BMSCs) into Cytomatrix™ scaffolds at different collagen-terpolymer contact times.

In this example, the density of the modified collagen-terpolymer complex is modulated by varying the contact time of the oppositely charged polymers used in the method of the present invention. The modified collagen and terpolymer as described in Example 1 are used.

For seeding pig BMSCs into scaffolds by encapsulation $1\times10^6$ cells/ml of pig BMSCs are mixed with 1.5 mg/ml of modified collagen and 100 µl of the cell-collagen mixture is seeded into each scaffold as described in Example 1. Encapsulation of the cells in the scaffold is carried out as described in Example 1 using different contact time (1, 5, 10, 20 and 30 min). The scaffolds are then transferred into spinner flasks for dynamic culturing at 2 rpm for 2 weeks.

Controls are established by conventional static seeding. $1\times10^6$ cells/ml of pig BMSCs are resuspended in culture medium and 100 µl of cell suspension is seeded into each scaffold. The scaffold is then incubated at 37° C. for 4 hours to allow for cell attachment before placing into spinner flasks for dynamic culturing.

The seeding efficiency is determined by quantifying the number of cells that are not encapsulated. Cells that are not entrapped in the scaffold after the complex coacervation reaction are collected and incubated with Accumax (Innovative Cell Technologies Inc. San Diego, Calif.) to digest away remnants of the collagen-terpolymer complex. The single cell suspension was then counted with a hemocytometer (Bright-Line Hemacytometer, Hausser Scientific Horsham, Pa.). The cell seeding efficiency is determined as:

$$\% \text{ seeding efficiency} = \frac{\text{No. of cells seeded} - \text{No. of cells not encapsulated}}{\text{No. of cells seeded}}$$

The viability of pig BMSCs in encapsulated scaffolds is assessed after 2 weeks of culture by Cell Tracker Green (CTG) and Propidium Iodide (PI) staining. Specimens are prepared by staining viable cells green with the fluorescent dye, CTG (Molecular Probes Inc., Oregon). The scaffolds are incubated at 37° C. with 20 µM CTG in culture medium for 30 minutes. After rinsing twice with PBS, each sample is then placed in 0.1 mg/ml Propidium Iodide solution (Molecular Probes Inc., Oregon) for 2 minutes at room temperature to stain dead cells red. The scaffolds are then rinsed twice in PBS and viewed under the confocal laser microscope (Olympus Fluoview 500) at 488 nm and 543 nm excitation.

A 300 µm optical section (with 10 µm step size) of pig BMSCs in Cytomatrix™ scaffold stained with CTG/PI is obtained. The images are processed with Image-Pro® Plus (Media Cybernatics Inc., MD, USA) to quantify the number of bright pixels in a 512×512 image for both green (live cells) and red (dead cells) channels. The total number of bright pixels for the respective channels in the 300 µm stack is then calculated. The percentage cell viability is calculated as:

$$\% \text{ viability} = \frac{\text{No. of green pixels in 300 µm stack}}{\text{No. of green \& red pixels in 300 µm stack}}$$

The use of encapsulation as a means to seeding pig BMSCs into the Cytomatrix™ scaffolds with the collagen-terpolymer charged polymer pair was able to improve seeding efficiency significantly. Seeding efficiency by conventional static seeding procedure was 54% while with the proposed method of encapsulation, significant improvement in seeding efficiency can be observed, ranging from 78% to 97% over the range of charged polymer contact time investigated (FIG. 7). A contact time of at least 5 minutes is required to achieve a seeding efficiency of higher than 90%.

Figure 8:
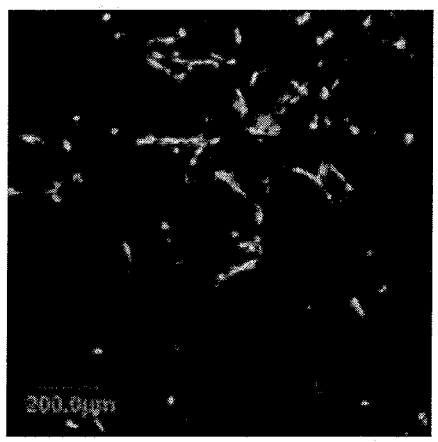
FIG. 8 shows the cell viability staining (CTG/PI) of pig bone marrow stroma cells encapsulated in Cytomatrix™ scaffolds with positively charged collagen and terpolymer after 2 weeks of dynamic culture in a spinner flask. Images shown are projections of a 300 µm optical section (z-axis, i.e. longitudinal axis of the cylindrical scaffold) onto a single plane (10× magnification). Contact time of the oppositely charged polymers in FIG. 8A was 1 min, in FIG. 8B 10 min and in FIG. 8C 30 min.
Figure 8:
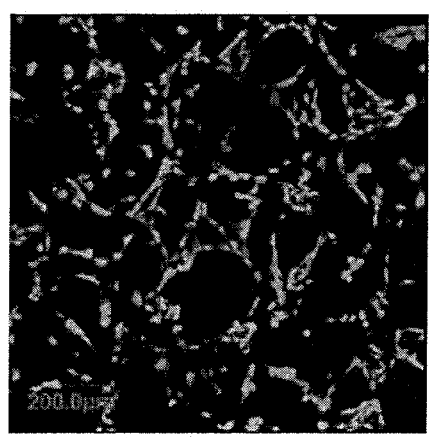
Figure 8:
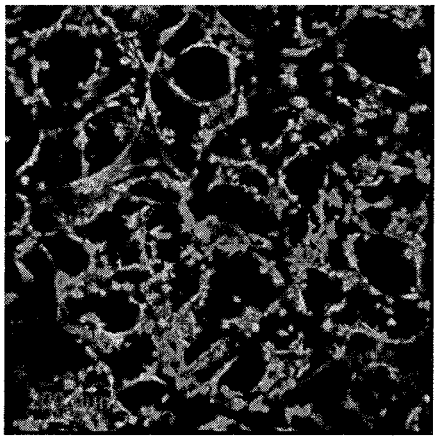
Figure 8:
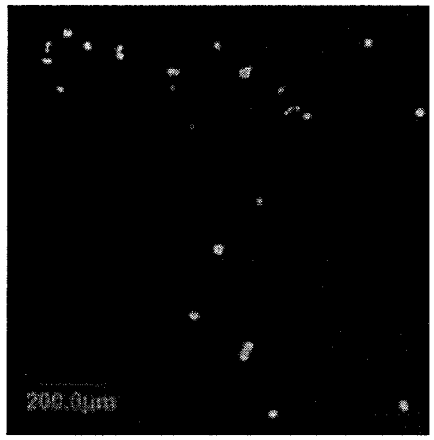
Figure 9:
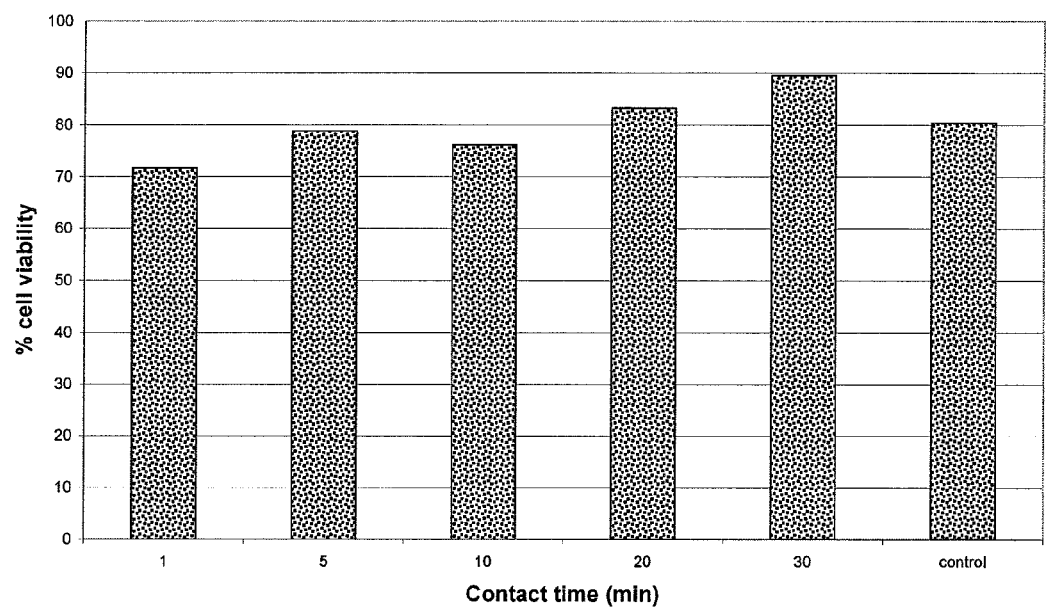
FIG. 9 shows the percentage of cell viability after two weeks of dynamic culture of pig bone marrow stroma cells in Cytomatrix™ scaffolds each encapsulated with positively charged collagen and terpolymer at different polymer contact times (for more details see Example 3).

Although encapsulation of cells in the three dimensional scaffolds is effective in seeding cells, it is imperative to assess whether the viability of the cells is affected by the encapsulation process. Here, $1\times10^6$ cells/ml of pig MSCs are seeded into Cytomatrix™ scaffolds by encapsulation at different contact time (1, 5, 10, 20 and 30 minutes) and cultured statically or dynamically for 2 weeks before assessing for cell viability. The results can be seen from FIGS. 8 and 9. In FIG. 8A, the contact time of the oppositely charged polymers is 1 min, in FIG. 8B 10 min and in FIG. 8C 30 min. FIG. 8D shows a control scaffold that is seeded by conventional static seeding (method). From the cell viability staining (FIG. 8), it can be observed that within the range of charged polymer contact time investigated, pig BMSCs are able to proliferate and cell viability is not compromised with a longer contact time in dynamic cultures (FIG. 9).

Example 4

This example illustrates the use of the complex coacervation reaction between methylated collagen as first charged polymer and terpolymer of HEMA-MMA-MAA as second charged polymer to manipulate the formation of polymer matrices which have an important bearing on cellular behavior. Collagen of different methylation degrees is used to complex coacervate with terpolymer to alter collagen matrix morphology to engineer microenvironments for optimal cell support. Two liver-derived model cell types, primary hepatocytes and HepG2 cell line are chosen to study the effect of matrix morphology on cellular functions. Primary hepatocytes represent primary cells that are highly sensitive, terminally differentiated and require specific chemical and topological extra-cellular matrix (ECM) cues for the maintenance of differentiated functions in vitro, while HepG2 is a hepatic cell line that represents transformed cell lines which can proliferate relatively easily in culture as long as no contact inhibition is encountered.

Collagen is modified to be cationic via methylation as described in Example 1. The degree of methylation is controlled by adjusting the reaction time and temperature. Briefly, the precipitated collagen is dissolved and stirred in acidified methanol for 4° C., 6 days (slightly methylated) and 23° C., 1 day (highly methylated), respectively, and the degree of methylation is characterized by capillary zone electrophoresis. The capillary zone electrophoresis (CE) has been used to develop a method for the quantification of the degree of collagen methylation.

Separations of different methylated collagens are performed on a CE-L1 System, from CE Resources Pte Ltd (Singapore). The polyvinyl alcohol (PVA) coated capillaries (50 µm ID×360 µm OD×70 cm length with 45 cm effective length) used are also obtained from CE Resources Pte Ltd (Singapore). Separations are run with 50 mM sodium phosphate buffer (pH 2.5) with 0.05% hydroxypropyl methyl cellulose (HPMC) at 21° C. Separation voltage is 22 kV and UV absorbance is detected at 200 nm. The collagen samples are introduced into the capillary by pressure (0.3 psi×15 s). PVA-coated capillaries are washed with distilled water for three minutes prior to the initial use. After initial conditioning, the coated capillaries are washed with distilled water for 1 min and 50 mM sodium phosphate buffer (pH 2.5) with 0.05% hydroxypropyl methyl cellulose (HPMC) for 3 min between each analysis. All chemicals used are either of analytical grade or highest available purity. Hydrochloric acid, sodium phosphate, methanol and sodium hydroxide are obtained from Merck & Co. (NJ, USA). HPMC (VISC. 2 wt % in water, 5 CPS) is bought from Sigma-Aldrich Co. (St. Louis, Mo., USA). Acetone is purchased from Tedla Company Inc (Fairfield, USA). All buffers and solutions are prepared with water purified through a Milli-Q system (Barnstead, Wis., USA).

Figure 12:
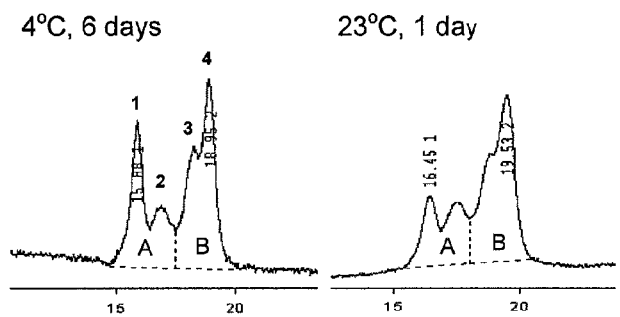
FIG. 12 illustrates the degree of collagen methylation characterized by the elution peaks of methylated collagen resolved by capillary electrophoresis. Based on this new method to quantify the degree of methylation as described in Example 4 the CE index was developed on the basis of the data obtained from FIG. 12. The CE index characterizes the relative growth in the downstream peaks as increased degree of methylation. The CE index is calculated by dividing the area of the downstream peaks over that of the upstream peaks (Area B/Area A).

The methylated collagens are separated into four major bands (FIG. 12), that change with different methylation reaction conditions. An increase in collagen methylation correlates with a relative increase in the sizes of the downstream peaks. To quantify the degree of the collagen methylation, a CE index was developed which characterizes the relative growth in the downstream peaks as increased degree of methylation. The CE index is calculated by dividing the area of the downstream peaks over that of the upstream peaks (Area B/Area A in FIG. 12). An increase in collagen methylation correlates with an increase in the CE index (Table 1). The CE index of slightly methylated collagen is between 0.9 and 1.7 whereas the CE index of highly methylated collagen is between 1.7 and 2.5. The oppositely charged polymer used to react with the modified collagen is terpolymer of HEMA-MMA-MAA that is synthesized as described in Example 1.

TABLE 1

Capillary electrophoresis (CE) indices for two collagen methylation reactions. Degree of collagen methylation is characterized by the elution peaks of methylated collagen resolved by capillary zone electrophoresis.

| Collagen methylation | CE Index (area of B over A) |
|---|---|
| 4° C., 6 days | 1.40 |
| 23° C., 1 day | 1.90 |

For characterization studies of collagen matrix formation, encapsulation of primary hepatocytes and HepG2 cells has been carried out according to the method described in Example 1. Confocal backscattering microscopy (Olympus Fluoview 500) is used to image the collagen matrix formed using a 60× water lens. Image-Pro Plus 4.5.1 is employed for the image processing and quantitative evaluation of matrix parameters.

For cell studies, hepatocytes are harvested from male Wistar rats by a two-step in situ collagenase perfusion as described previously (Seglen P. O., Methods Cell Biol. 1976, Vol. 13, P. 29-83) with some modifications. The cells are suspended in methylated collagen at a cell density of $5\times10^6$/ml (hepatocytes) or $8\times10^5$/ml (HepG2) before being filled into the scaffold and contacted with terpolymer. The hepatocytes and HepG2 cells supported by the collagen matrix are cultured in Hepatozym-SFM (GIBCO Laboratories) and DMEM supplemented with fetal calf serum (10%) and HEPES (1 g/l) respectively in 37° C., 5% $CO_2$ humidified atmosphere. Hepatocytes detoxification functions are accessed by the 7-ethoxyresorufin-O-dealkylation (EROD) and 7-ethyoxycoumarin-O-deethylase (ECOD) activities of hepatocytes. Briefly, these involves the addition of 39.2 µM 7-ethoxyresorufin for 5 h (EROD) and 0.26 mM 7-ethyoxycoumarin for 3 h (ECOD), and the quantification of their metabolic products by confocal fluorescent microscopy (EROD) and High Performance Liquid Chromatography (HPLC) (ECOD). The proliferation of HepG2 cells over time is monitored by microscopy (Olympus Fluoview 500).

Figure 11:
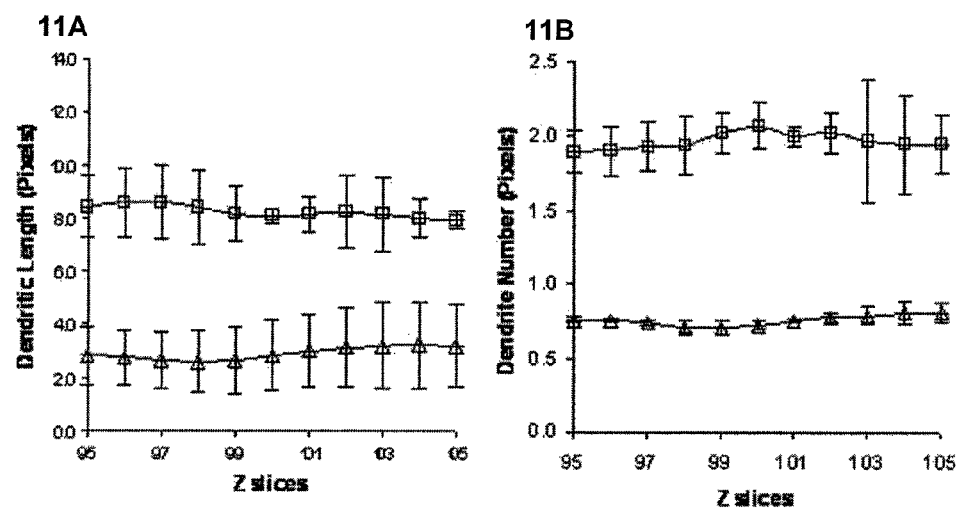
FIG. 11 shows the result of quantitative analyses of collagen matrix morphology (Example 4): (A) Mean dendritic length per node; (B) Mean dendrite number per node [(□) Slightly methylated collagen; (Δ) Highly methylated collagen].

Thin, fragmented matrices are formed by highly methylated collagen (FIG. 10A) upon reaction with terpolymer, in contrast to the thick, connected matrices formed by slightly methylated collagen (FIG. 10B). To quantify the effect of collagen methylation on matrix morphology, the mean dendritic length, defined as the average sum of the length of dendrites connected to each node per slice, and mean dendrite number, defined as the average sum of dendrites connected to each node per slice, are plotted for the ten centre slices in the z-stack (FIGS. 11A, 11B). From FIG. 11, the mean dendritic length and dendrite number for the highly methylated collagen (Δ), representative of fiber length and branching within the matrix respectively, are consistently below that of the slightly methylated collagen (□). Therefore, an increase in collagen methylation can be correlated with more fragmented matrix morphology.

Figure 14:
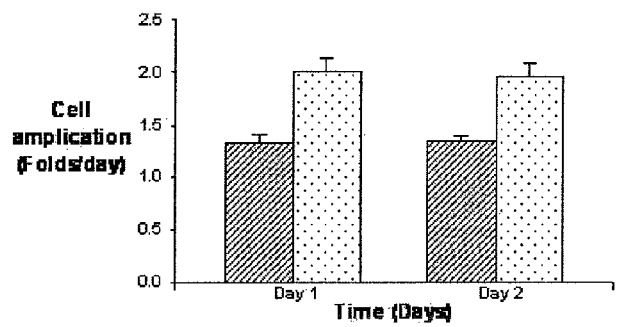
FIG. 14 illustrates the effect of collagen methylation (Example 4) on HepG2 proliferation. [(▒) Slightly methylated collagen (CE index 1.4); (■) Highly methylated collagen (CE index 1.9)].

The detoxification functions of hepatocytes, indicated by their EROD and ECOD activities (FIGS. 13A, 13B), are significantly higher for all 4 days of culture when supported by the more connected matrix formed by slightly methylated collagen (▨) compared to the matrix formed by highly methylated collagen (■). The ECOD scheme which employs HPLC for the measurement of metabolic products is a more precise assay that tests for the monooxygenase activities of more cytochrome P450 enzymes (CYP1A1, CYP2A6, CYP2C8-9, CYP2E1), but both EROD and ECOD assays detect significant differences in cytochrome enzyme activities in the two microenvironments. In contrast, HepG2 cell amplification in highly methylated collagen, defined as the ratio of cell number in microcapsule in $Day_{n+1}$ over $Day_n$, is greater than that of slightly methylated collagen by 1.5 times. On average, cell amplification for highly methylated (■) and slightly methylated collagen (▨) is 2 folds/day and 1.3 folds/day respectively (FIG. 14). Thus, the connected nano-fibers of the matrix formed by slightly methylated collagen enhanced the differentiated functions of hepatocytes, while the fragmented nano-fibers formed by highly methylated collagen favored the proliferation of HepG2 cells.

Therefore, the proposed method of controlling collagen matrix formation by complex coacervation has been demonstrated to be capable of modulating matrix morphology to provide differential levels of cellular support. In particular, it has been shown that precise control of the matrix structure supporting live cells is important in cellular support and functions because hepatocyte functions and HepG2 proliferation are selectively augmented in microenvironments with different matrix connectivity.

Example 5

The following example demonstrates the encapsulation of human dermal fibroblasts (HDF) into Cytomatrix™ scaffolds by the complex coacervation between half N-acetylated chitosan and terpolymer of hydroxylethyl methacrylate-methyl methacrylate-methyl acrylic acid (HEMA-MMA-MAA) using different contact times.

As in the previous examples Cytomatrix® scaffolds are used as model for three dimensional cell growth matrices to assess the feasibility of encapsulating HDF by the complex coacervation between half N-acetylated chitosan and terpolymer. The terpolymer HEMA-MMA-MAA is synthesized as described in Example 1. 3% HEMA-MMA-MAA was used to encapsulate the cells in the three dimensional scaffolds.

400 kDa half N-acetylated chitosan is synthesized, purified and dissolved with PBS to 0.5%. Half N-acetylated chitosan is prepared from 15.3% N-acetylation chitosan by N-acetylation with acetic anhydride, according to the method described by Kubota N, et al. (Carbhydr. Res., 2000, Vol. 324, P. 268-274). Briefly, 15.3% N-acetylated chitosan (1.5 g) with various molar masses are dissolved in 10% acetic acid solution (250 ml) and acetic anhydride is added accordingly to obtain a molar ratio of acetic anhydride to glucosamine (GlcN) of 10. After stirring at ambient temperature for 250 minutes, 1N NaOH solution is added to the solution until the pH reached 8-9 to stop the acetylation reaction. The reaction mixture is then dialyzed against de-ionized water repeatedly to remove excess free ions, and then lyophilized. 400 kDa and 150 kDa 15.3% N-acetylated chitosans are used as purchased from manufacturer. 80 kDa 15.3% N-acetylated chitosan is prepared by radical degradation (Bartkowiak, A. and Hunkeler, D., Chem. Mater., 1999, Vol. 11, P. 2486-2492) from the 400 kDa 15.3% N-acetylated chitosan. The molar mass of degraded chitosan is determined by gel permeable chromatography to be ~80 kDa.

HDF are derived from explant cultures of human skin samples and cultured using Dulbecco's modified Eagle medium (DMEM), low glucose (Gibco Grand Island, N.Y.) supplemented with 10% fetal bovine serum (FBS). The cultures are cultured to about 90% confluence before passaging. Passage 2-9 cells are used in the experiments.

$1 \times 10^6$ cells/n/1 of HDF are mixed with 0.5% of half N-acetylated chitosan and 100 µl of the cell-chitosan mixture are seeded into each scaffold. Encapsulation of the cells in the scaffold is carried out as described in Example 1 using different contact times. The scaffolds are then transferred into spinner flasks for dynamic culturing at 2 rpm for 1 week. Controls are established by conventional static seeding. $1 \times 10^6$ cells/ml of HDF are resuspended in culture medium and 100 µl of cell suspension is seeded into each scaffold. The scaffold is then incubated at 37° C. for 2 hours to allow for cell attachment before placing into spinner flasks for dynamic culturing.

The seeding efficiency is determined as described in Example 3 with slight differences. Instead of Accumax to digest away remnants of the polymer complex trypsin is used.

The viability of HDF in encapsulated scaffolds is assessed after 1 week of culture by Cell Tracker Green (CTG) and Propidium Iodide (PI) staining as described in Example 3. Dead cells are stained for 5 minutes with propidium iodide solution instead of 2 minutes as described in Example 3.

As described in Example 3, a 300 µm optical section (with 10 Mm step size) of HDF cells in Cytomatrix™ scaffold stained with CTG/PI is obtained and analyzed via confocal laser microscopy. The viability is calculated according to the formula given in Example 3.

Figure 15:
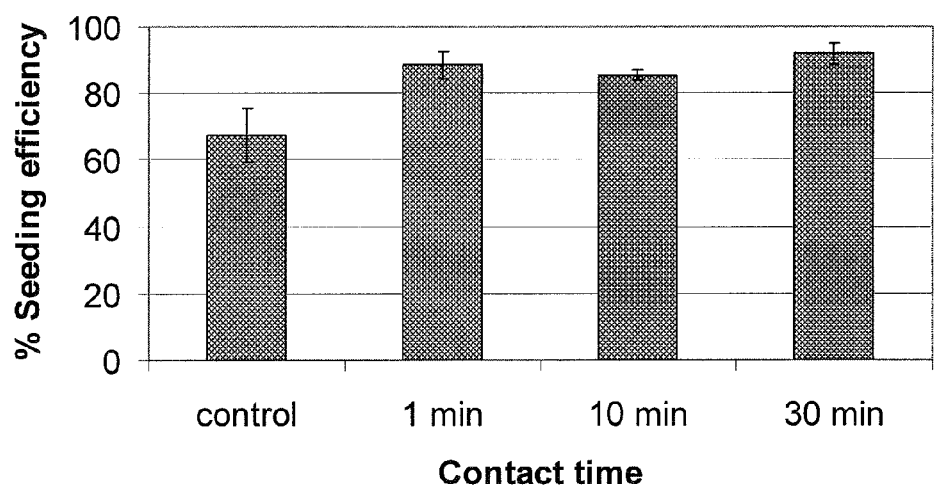
FIG. 15 shows the percentage seeding efficiency of HDF in Cytomatrix™ scaffolds by encapsulation of half N-acetylated chitosan and terpolymer at different polymer contact times (for more details see Example 5).

The seeding efficiency of HDF in Cytomatrix™ scaffolds is ameliorated by encapsulating the scaffold with half N-acetylated chitosan and terpolymer (FIG. 15). For the contact time investigated, the seeding efficiencies ranged from 85.3% to 91.8% which are significantly higher as compared to that of conventional seeding.

Figure 16:
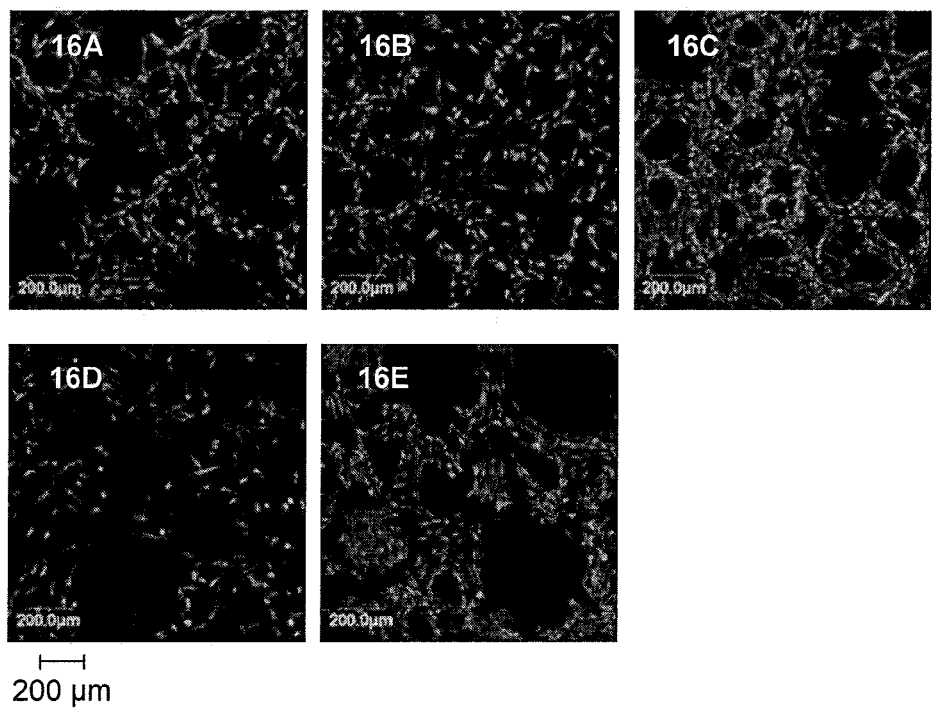
FIG. 16 shows the cell viability staining (CTG/PI) of HDF cells encapsulated in Cytomatrix™ scaffolds with half N-acetylated chitosan and terpolymer after 1 week of dynamic culture in a spinner flask. Images shown are projections of a 300 µm optical section (z-axis, i.e. longitudinal axis of the cylindrical scaffold) onto a single plane (10× magnification). Contact time of the oppositely charged polymers in FIG. 16A was 1 min, in FIG. 16B 10 min, in FIG. 16C 30 min.

From the viability staining, it can be observed that for the range of contact time investigated, the viability of HDF are not compromised (FIG. 16). FIG. 16A shows stained cells after 1 min contact time of the reacting polymers. FIG. 16B shows stained cells after 10 min contact time. FIG. 16C shows stained cells after 30 min contact time and FIGS. 16D and 16E show different sides of a control scaffold seeded by conventional static seeding (methods). From these pictures it can be observed that despite the enhanced initial cell number for the encapsulated scaffolds, the cell number is not significantly higher than that of the control scaffold after 1 week of culture. However, it should be noted that the distribution of the cells within encapsulated scaffolds is much more uniform than that of the control scaffold (FIGS. 16D and 16E).

Example 6

The following example describes the uniform distribution of cells encapsulated in scaffolds using the method of the present invention. Therefore, human dermal fibroblasts (HDF) are encapsulated into Cytomatrix™ scaffolds by the complex coacervation between modified collagen and terpolymer of hydroxylethyl methacrylate-methyl methacrylate-methyl acrylic acid (HEMA-MMA-MAA).

Collagen and terpolymer (HEMA-MMA-MAA) are used as described in Example 1. HDF cells were obtained as described in Example 5.

$5 \times 10^5$ cells/ml of HDFs are mixed with 1.5 mg/ml of modified collagen and 100 µl of the cell-collagen mixture is seeded into each scaffold. Encapsulation is carried out as described in Example 1. After 10 minutes, the complex coacervation reaction is quenched with PBS solution. The scaffolds are then transferred into spinner flasks for dynamic culturing at 2 rpm for 1 week. Controls were established by conventional static seeding. $5 \times 10^5$ cells/ml of cells are resuspended in medium and 100 µl of cell suspension is seeded into each scaffold. The scaffold is then incubated at 37° C. for 4 hours to allow for cell attachment before placing into spinner flasks for dynamic culturing. The cell viability is assessed as described in Example 5.

Figure 17:
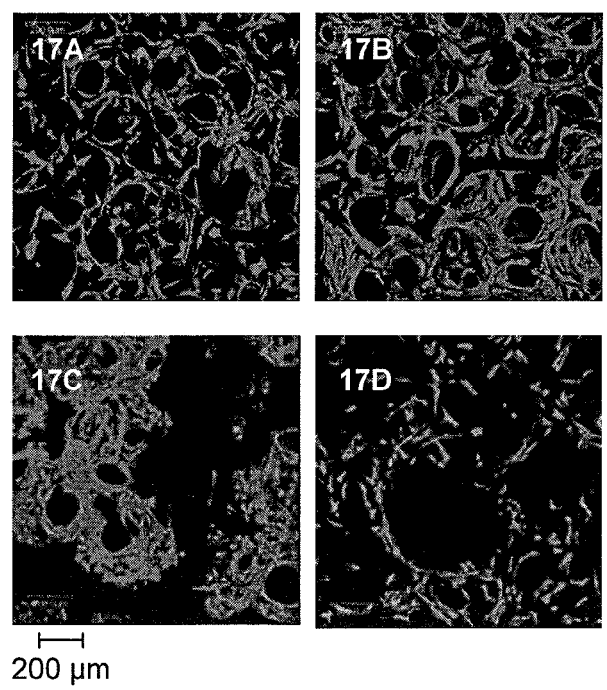
FIG. 17 shows the cell viability staining (CTG/PI) of HDF cells encapsulated in Cytomatrix™ scaffolds with modified collagen and terpolymer (HEMA-MMA-MAA) after 1 week of dynamic culture (Example 6). Images shown are projections of a 300 µm optical section (z-axis, i.e. longitudinal axis of the cylindrical scaffold) onto a single plane (10× magnification).

From the viability staining (FIG. 17), it can observed that there is no significant increase in cell number for the encapsulated scaffolds after 1 week of culture. This may be due to the fact that fibroblasts have a relatively short doubling time as compared to other cell types, such as bone marrow stromal cells and can easily compensate for an initial lower seeding efficiency. However, the uniformity of the cells within the encapsulated scaffold is much higher (FIGS. 17A and B) than that of the control (FIGS. 17 C and D).

What is claimed is:

1. A method for encapsulating at least one cell in a biologically compatible scaffold comprising:
    (a) providing a first substrate coated with a first charged polymer;
    (b) placing a scaffold comprising at least one cell embedded in a second charged polymer having an electrical charge opposite to that of the first charged polymer onto the first charged polymer on the first substrate;
    (c) placing a second substrate coated with a third charged polymer to form a sandwich structure with the first substrate and the scaffold arranged therebetween, wherein the first polymer and the third polymer are of the same electrical charge; and
    d) forming by complex coacervation of the second charged polymer with the first and third charged polymers a membrane formed of a polymer complex, wherein the polymer complex encapsulates the at least one cell therein.

2. The method of claim 1, wherein an attachment-dependent cell is used as the at least one cell.

3. The method of claim 1, wherein an attachment-independent cell is used as the at least one cell.

4. The method of claim 1, wherein the charged polymers form polymer complexes being permeable to substances necessary to sustain the normal metabolic functions of the at least one cell and to products released by the at least one cell.

5. The method of claim 1, wherein the first charged polymer and the third charged polymer are identical.

6. The method of claim 1, wherein the second charged polymer is selected from the group consisting of chitosan, polyanionic alginate, negatively or positively charged collagen, carboxymethylcellulose (CMC) and polyanionic alginate.

7. The method of claim 1, wherein the first charged polymer is selected from the group consisting of terpolymer, $Ca^{2+}$, chondroitin sulfate A-chitosan and polycationic poly(L-lysine).

8. The method of claim 6, wherein the positively charged collagen is used as said second charged polymer.

9. The method of claim 8, wherein a negatively charged terpolymer comprising at least one of acrylic acid and methacrylic acid and at least one of hydroxyethyl methacrylate and hydroxylpropyl methacrylate is used as said first charged polymer.

10. The method of claim 9, wherein a terpolymer consisting of 25% 2-hydroxyethyl methacrylate, 25% methacrylic acid and 50% methyl methacrylate (HEMA-MAA-MMA) is used as said first charged polymer.

11. The method of claim 9, wherein the degree of cross linking of the polymer complex formed by the reaction of the positively charged collagen with said terpolymer is controlled by varying the reaction time (contact time) between said polymers.

12. The method of claim 1, wherein the degree of cross linking of the polymer complex can be altered by varying the charge density of the polymers.

13. The method of claim 12, wherein a slightly methylated polymer and/or a highly methylated polymer is used, wherein the slightly methylated polymer has a charge density of between 0.9 and 1.7 CE and the highly methylated polymer has a charge density of between 1.7 and 2.5 CE.

14. The method of claim 1, wherein the second substrate coated with the third charged polymer is contacted with the first substrate coated with the first charged polymer and the scaffold arranged therebetween for about 30 seconds to about 1 hour.

15. The method of claim 1, wherein the first substrate comprises a material selecting from the group consisting of glass, plastic, silicon, a metal and a metal oxide.

16. The method of claim 2, wherein the attachment-dependent cell is selected from the group consisting of a bone marrow stroma cell, a calvarial osteoblast, a Langerhans cell, a hepatocyte, a chondrocyte, a cardiac myocyte, a sinusoidal endothelial cell, a dermal fibroblast, a kerotinocyte and an oligodendrocyte.

17. The method of claim 3, wherein the attachment-independent cell is selected from the group consisting of a hematopoetic stem cell, a T-lymphocyte, a macrophage and a neutrophil.

* * * * *